United States Patent [19]
Kurimoto et al.

[11] Patent Number: 5,153,162
[45] Date of Patent: Oct. 6, 1992

[54] CATALYST FOR THE PRODUCTION OF METHACRYLIC ACID

[75] Inventors: Ikuo Kurimoto; Hideto Hashiba; Hideo Onodera, all of Himeji; Yukio Aoki, Hyogo, all of Japan

[73] Assignee: Nippon Shokubai Kagaku Kogyo Co., Ltd., Osaka, Japan

[21] Appl. No.: 574,139

[22] Filed: Aug. 29, 1990

[30] Foreign Application Priority Data

Aug. 29, 1989 [JP] Japan .................. 1-220380
Aug. 6, 1990 [JP] Japan .................. 2-206857

[51] Int. Cl.⁵ .............. B01J 27/16; B01J 27/185; B01J 27/19; B01J 27/198
[52] U.S. Cl. .................. 502/209; 502/211; 502/212
[58] Field of Search .............. 502/211, 209, 212

[56] References Cited

U.S. PATENT DOCUMENTS

| | | | |
|---|---|---|---|
| 4,259,211 | 3/1981 | Krabetz et al. | 252/443 |
| 4,305,843 | 12/1981 | Krabetz et al. | 502/209 X |
| 4,547,588 | 3/1981 | Khoobiar | 502/211 X |
| 4,558,028 | 12/1985 | Tsuneki et al. | 502/211 |
| 4,558,029 | 12/1985 | Paparizos et al. | 502/211 |
| 4,621,072 | 11/1986 | Arntz et al. | 502/212 X |

FOREIGN PATENT DOCUMENTS

| | | |
|---|---|---|
| 0051348 | 12/1982 | European Pat. Off. . |
| 0265733 | 4/1988 | European Pat. Off. . |
| 2626887 | 12/1977 | Fed. Rep. of Germany . |
| 2046252 | 11/1980 | United Kingdom . |

*Primary Examiner*—W. J. Shine
*Attorney, Agent, or Firm*—Sherman and Shalloway

[57] ABSTRACT

A catalyst for the production of methacrylic acid composed of an inert carrier and a catalytically active substance. The catalytically active substance layer being composed of oxides represented by the following formula (I)

$$Mo_aP_bA_cB_dC_eD_fO_x \quad (I)$$

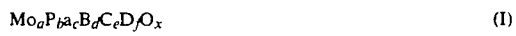

where Mo represents molybdenum, P represents phosphorus, A represents at least one element selected from arsenic, antimony, germanium, bismuth, zirconium, cerium and selenium, B is at least one element selected from copper, iron, chromium, nickel, maganese, cobalt, tin, silver, zinc, palladium, rhodium and tellurium, C represents at least one element selected from vanadium, tungsten and niobium, D represents at least one element selected from alkali metals, alkaline earth metals and thallium, and O represents oxygen, a, b, c, d, e, f and x respectively represent the atomic ratios of Mo, P, A, B, C, D and O, and when $a=12$, $b=0.5-4$, $c=0-5$, $d=0-3$, $e=0-4$, and $f=0.01-4$, and x is a numerical value determined by the oxidation states of these elements. The catalytically active substance layers are formed by mixing compounds of the elemental components of the oxides of formula (I), as required, heating them to prepare a slurry or a solution, spraying the slurry or solution onto the inert carrier, and calcining the inert carrier so sprayed.

3 Claims, No Drawings

CATALYST FOR THE PRODUCTION OF METHACRYLIC ACID

This invention relates to a catalyst for the production of methacrylic acid. More specifically, this invention relates to an oxidation catalyst suitable for producing methacrylic acid by vapor phase catalytic oxidation reaction or vapor phase catalytic oxidative dehydrogenation reaction of methacrolein, isobutylaldehyde and isobutyric acid, or a mixture of these or oxidizing a methacrolein-containing gas obtained by oxidizing a starting material such as isobutylene etc.

For production of methacrylic acid with good efficiency by vapor-phase catalytic oxidation reaction of methacrolein, etc., various improved catalysts have been proposed. These improvements mainly relate to the components constituting the catalyst and the selection of their proportions. Some of them relates to the specifying of the properties of the catalysts and the method of catalyst preparation.

Some proposals have been made on the properties of the catalysts, for example the specific surface area, the pore volume, pore diameters, etc. of the catalyst itself. But the resulting catalysts are insufficient in performance, and none have been found to be satisfactory.

For example, Japanese Laid-Open Patent Publications Nos. 116022/1974 and 37710/75 describe respectively that the preferred specific surface areas of the catalysts are 0.01 to 5 $m^2/g$ and 0.01 to 50 $m^2/g$. However the catalysts whose specific surface area is defined within the above range might have a high reaction temperature or a low selectivity of methacrylic acid, and are not industrially satisfactory.

In regard to the specific surface area and the pore volume, Japanese Patent Publication No. 13876/1979 discloses a method of molding a catalyst having a specific surface area of 4 to 20 $m^2/g$ and a pore volume of 0.08 to 0.5 ml/g and containing as essential components phosphorus, molybdenum and X where X is at least one metal selected from thallium, metals of Groups IA and II by means of a tumbling granulator. But as far as the embodiment practice of this invention is examined, the reaction temperature is high, and the catalyst is not satisfactory as an industrial catalyst.

On the other hand, with regard to the method of preparing the catalyst, supported catalysts were proposed because particularly, a molded catalyst does not have a sufficiently high strength, and has inferior wear resistance. For example, Japanese Laid-Open Patent Publication Nos. 153889/1977, 50116/1978, 32734/1982, 37050/1981, 48143/1985 and 12758/1984 disclose these supported catalysts. These patent documents disclose a method of supporting the catalytically active substances, which comprises pre-calcining precursors, pulverizing the precursors, and then depositing the pulverized product. Elsewhere, these patent documents only disclose a method of specifying the properties of a carrier or a method of preparing chemicals.

The reaction of producing methacrylic acid by vapor-phase catalytic oxidation reaction or vapor-phase catalytic oxidative dehydrogenation reaction of methacrolein, isobutylaldehyde, isobutylic acid or a mixture of two or more of them is an exothermic reaction where the amount of heat generated is extremely large, and heat accumulation in the catalytically active substance layer is large. In particular, in localized abnormally high temperature portions called "hot spots", not only the yield decreased owing to the excessive oxidation reaction, but also the life of the catalyst becomes short owing to the degradation of the catalyst caused by the heat loading. Accordingly, it is desirable to decrease heat accumulation in the catalytically active substance layer and inhibit the consecutive reaction of the resulting methacrylic acid in order to produce methacrylic acid at a high yield and a high selectivity. To achieve this, it is necessary to reduce the thickness of the catalytically active substance layer. However, by the conventional depositing method or the immersion depositing method previously used for the preparation of a catalyst for production of methacrylic acid, it is difficult to form the catalytically active substance layer in the inert carrier or even when it is formed there, it peels off easily.

As a catalyst for production of methacrylic acid, its catalyst strength etc. become a problem in its industrial practice, and it is desirable to form a catalyst having excellent wear resistance and peeling resistance. However, by the conventional impregnation deposition method or the immersion deposition method, it is difficult to form a firm catalytically active substance layer, and an industrially satisfactory catalysts for the production of methacrylic acid cannot be obtained.

On the other hand, when a process (to be referred to as a "continuous process" comprising a reaction in which at least one starting material selected from isobutylene, tert-butanol and methyl tert-butyl ether is oxidized catalytically in the vapor phase to form methacrolein (pre-stage reaction) and a reaction of oxidizing this methacrolein-containing mixed gas directly oxidized to form methacrylic acid (latter-stage reaction) is employed, it is known that the unreacted material or high-boiling by-products (these may be generically called "impurities") in the gas from the pre-stage reaction (to be referred to as the "outlet gas of the pre-stage reaction") suppress the activity of the catalyst for the production of methacrylic acid used in the latter-stage reaction.

Accordingly, a catalyst for the commercial production of methacrylic acid especially preferably should show excellent catalyst performances with high activity and high selectivity, and especially desirably, should not be vulnerable to inhibition of activity by the impurities in the outlet gas in the pre-stage reaction in the above continuous process.

One object of this invention is to provide a catalyst for the production of methacrylic acid in a high yield and a high selectivity.

Another object of this invention is to provide a catalyst for the production of methacrylic acid which reduces heat accumulation in the reaction of forming of methacrylic acid, inhibits the consecutive reaction of the resulting methacrylic acid, and prevents the catalyst's degradation by thermal loading.

Another objects of this invention is to provide a catalyst for suitable for commercial production of methacrylic acid having excellent wear resistance, peel resistance and mechanical strength.

Another object of this invention is to provide a catalyst for production of methacrylic acid showing high activity, and high selectivity and excellent catalytic performance, which even when used in the later stage reaction of the continuous process, is little inhibited in activity by the impurities in the outlet gas in the pre-stage reaction.

The present inventors found that (1) a specified catalytically active substance layer is supported onto an inert carrier, and this catalytically active substance layer is maintained in a thin layer; (2) the deposition of the specific catalytically active substance layer onto the inert carrier, and to maintain the catalytically active substance in a thin layer can be achieved by a novel baking deposition method instead of the impregnation depositing method or the immersion deposition method used in the conventional preparation of a catalyst for the production methacrylic acid; and (3) according to this baking deposition method, a catalytically active substance layer having a specific surface area, a pore volume and a pore diameter within specific ranges is obtained and by using a catalyst having these particular specific surface area, pore volume and pore diameter, methacrylic acid can be produced in a high yield and a high selectivity. This finding has led to the completion of this invention. Thus, according to this invention, there is provided a catalyst for the production of methacrylic acid composed of an inert carrier and a catalytically active substance layer deposited on the carrier, the catalytically active substance layer being composed of oxides represented by the following formula (I)

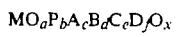

$$Mo_aP_bA_cB_dC_eD_fO_x \quad (I)$$

where Mo represents molybdenum, P represents phosphorus, A represents at least one element selected from arsenic, antimony, germanium, bismuth, zirconium, cerium and selenium, B is at least one element selected from copper, iron, chromium, nickel, manganese, cobalt, tin, silver, zinc, palladium, rhodium and tellurium, C represents at least one element selected from vanadium, tungsten and niobium, D represents at least one element selected from alkali metals, alkaline earth metals and thallium, and 0 represents oxygen, a, b, c, d, e, f and x respectively represent the atomic ratios of Mo, P, A, B, C, D and 0, and when a=12, b=0.5-4, c=0-5, d=0-3, e=0-4, and f=0.01-4, and x is a numerical value determined by the oxidation states of these elements.

The catalytically active substance layers are formed by mixing compounds of the elemental components of the oxides of formula (1), as required, heating them to prepare a slurry or a solution, spraying the slurry or solution onto the inert carrier, and calcining the inert carrier having deposited the slurry or solution thereon.

The catalyst of this invention for the production of methacrylic acid is composed of an inert carrier and a catalytically active substance layer deposited on the inert carrier. The inert carrier may be any known carriers which are(is) normally used such as silicon carbide, silica, alpha-alumina, silica-alumina, titania, and refractory materials. There is no particular restriction on the shape of the inert carrier. It may be spherical, or in the shape of pellet or ring-like. In particular, a spherical carrier with a diameter of about 3 to 10 mm, or a pellet-like carrier or a ring-like carrier having an outside diameter of about 3 to 10 mm and a length about 0.3 to 1.7 times the outside diameter are especially preferably used.

The catalytically active substance layer is composed of oxides represented by the formula (1). This catalytically active substance layer may be formed by mixing compounds containing Mo, P, A, B, C or D element components of the oxides of formula (1) as the starting material of the catalyst, as required, heating them to prepare a slurry or a solution, spraying the slurry or solution on the inert carrier, and thereafter calcining the inert carrier (to be referred to as, the method of forming the catalytically active substance layer; baking deposition method).

There is no particular restriction on the compounds containing elemental components as the starting compounds. They may be any oxides which contain the respective elemental components, compounds which form oxides by calcination. Examples of compounds which form oxides by calcining are hydroxides, metallic acids, nitrates, carbonates, ammonium salts, acetate and formates.

Specific examples of the molybdenum-containing compounds include molybdenum trioxide, ammonium paramolybdate, molybdic acid, phosphomolybdic acid, and phosphovanadomolybdic acid. Specific examples of the phosphorus-containing compound may include, for example, ortho-phosphoric acid, metal-phosphophoric acid, phosphorus acid, monoammonium phosphate, and diammonium phosphate.

Compounds containing two or more of the above elemental components may be used.

According to the baking deposition method of this invention, compounds containing the above elemental components are added to the medium, and further, as required, heated to prepare a slurry or a solution. Usually, water is used as the medium, and organic solvents such as alcohols or acetone may also be used. The above slurry or the solution may contain ammonium nitrate, cellulose, starch, polyvinyl alcohol, and stearic acid, etc. in order to adjust the specific surface area, the pore volume and the pore size distribution of the catalytically active substance layer with good reproducibility, or as a powdery binder. To reduce the degree of powderization of the catalyst, whiskers, glass fibers, etc. may be added.

The slurry or solution may be directly used as it is. Or the slurry or the solution is first concentrated and dried to a solid. Then, it may be dried, calcined and pulverized, and the resulting powder may be dispersed or dissolved again in water and used.

The solids concentration of the starting materials of the catalyst in the slurry or the solution is usually 50 to 500 g/liter.

According to the baking deposition method in this invention, the above slurry or solution is sprayed onto the inert carrier to form a deposited layer. This deposited layer may preferably be formed in a rotary furnace heated externally. Specifically, the inert carrier is put into the rotary furnace kept at 100° to 400° C., preferably 100° to 250° C. The inert carrier is pre-heated to this temperature, and then while rotating the rotary furnace, by such means as a sprayer, the slurry is sprayed onto the inert carrier to form a deposited layer of a uniform thickness.

According to the baking deposition method of this invention, the above deposited layer is finally dried as required, and calcined in an air stream or in a nitrogen stream at 200° to 600° C., preferably at 300° to 500° C. to form a catalytically active substance layer which is composed of oxides of formula (1).

The amount of the catalytically active substances deposited on the inert carrier after baking is usually 5 to 100 g, especially 10 to 50 g, per 100 ml of the carrier. If it is less than 5 g, the catalytically active substance layer is too thin so that the catalyst activity is low. On the other hand if it exceeds 100 g, the catalytically active substance layer becomes thick, and thin film formation intended by this invention cannot be achieved.

The catalytically active substance layer may be of a single layer structure or of a multilayer structure. If the catalytically active substance layer is of a multilayer structure which is composed of an inside layer which is superior in respect of catalyst performance but is susceptible to influences of impurities and of an outside layer having a weak force of impurities and having little inhibited oxidizing ability of methacrolein by the adsorption of impurites, the influences of the impurities in the outlet gases in the pre-stage reaction can be minimized when it is used in the latter stage of the continuous process.

Accordingly, a methacrylic acid production catalyst having a catalytically active substance layer of a multilayer structure, as compared with a methacrylic acid production catalyst having a catalytically active substance layer of a single layer structure, can exhibit an excellent performance in oxidizing a gaseous mixture containing methacrolein containing impurities and can be especially used effectively as a catalyst for use in a later stage reaction of the continuous process.

The catalytically active substance layer of the multilayer structure can be formed by mixing compounds containing the elemental components of the oxides of formula (1), and if required, heating the mixture to form a slurry or a solution in spraying this slurry or a solution on to an inert carrier, two or more slurries or solutions having different compositions are prepared, and can be successively sprayed onto the inert carrier, followed by baking.

Accordingly, the catalytically active substance layer of the multilayer structure are composed of oxide layers having different compositions. The "oxides having different compositions" as termed herein means not only within the definition of formula (1), constituent elemental components differ, but also the constituent elemental components are the same but have different atomic ratios. And as layers which constitute the catalytically active substance layers do not all have to have different compositions. To achieve the foregoing object effectively or optimize the catalyst performance, an operation of spraying two or more slurries or solutions may be repeated one or a plurality of times so that a plurality of layers of the same composition may exist such that a catalytically active substance layer of the multilayer structure may be formed by mixing the components containing respective elemental components of the oxides of formula (1), and as required, heated to prepare a slurry or a solution. In spraying two or more slurries or solutions having different compositions, and successively sprayed on the inert carrier and repeating this operation.

The calcination for the formation of a catalytically active substance layer of multilayer structure may be performed for each layer, but it may be carried out after all layers are sprayed and formed.

Of methacrylic acid production catalysts of a single layer or a multilayer structure, catalysts whose specific surface layer, pore volume and pore diameter distribution which are within the following ranges are preferred.

Specific surface area = 1 to 20 m²/g
Pore volume = 0.1-1 ml/g
Pore diameter distribution =

-continued

Pore diameters in the range of 1 to 10 micrometers 20-70%
Pore diameter in the ranges of 0.5 to less than 1 micrometer not more than 20%
Pore diameters in the range of 0.1 to 0.5 micrometer 20 to 70%

The specific surface area of the catalytically active substance layer in this invention was measured by a total automated surface area measuring device 4-Sorp (a product of Yuasa Ionics Co., Ltd/, and is 1 to 20 m²/g preferably 3 to 15 m²/g. If the specific surface area is less than 1 m²/g, its catalytic activity is too low. On the other hand, if it exceeds 20 m²/g, the selectivity of methacrylic acid is lowered and is undesirable. The pore volume was determined by a mercury penetrating-type porosimeter (autopore 9200 type made by Shimadzu Seisakusho and is within the range of 0.1 to 1 ml/g, preferably 0.2 to 0.8 ml/g If it is less than 0.1 ml/g, the catalyst activity is too low. On the other hand, if the, pore volume exceeds 1 ml/g, the selectivity of methacrylic acid decreases and it is undesirable from the standpoint of mechanical strength such as wear resistance and peel resistance.

The pore diameter distribution is determined by using the same mercury penetration porosimeter used in the measurement of the pore volume. The volume occupied by pores having pore diameters of 1 to 10 micrometers is 20 to 70 of the total pore volume, preferably 25 to 50%. The volume which is occupied by pores having pore diameters in the range of 0.5 to less than 1 micrometer is not more than 20% of the total pore volume, preferably not more than 15%. The volume which occupied by pores having pore diameters in the range of 0.1 to less than 0.5 micrometer is 20 to 70% of the total pore volume, preferably 40 to 65%.

Usually, a pore having a fine pore diameter greatly contributes to the specific surface area and pore volume. From the standpoint of the activity or selectivity of methacrylic acid production, the increase alone of the proportion of pores having a small pore diameter is insufficient. The copresence of pores having a relatively large diameter of 1 to 10 micrometers improves the properties of the catalyst.

If the specific surface area, the pore volume and the pore diameter distribution of the catalytically active substance layer are adjusted simultaneously within the above specified range, the objects of this invention are very effectively achieved.

According to the baking deposition method, it is easy to form a catalytically active substance layer having a specific surface area, a specific pore volume and a specific pore diameter distribution within these specific ranges. Furthermore, since according to the baking deposition method of this invention, a catalytically active substance layer having a specific surface area, these specific ranges can be formed with good reproducibility, a catalyst having uniform properties can be obtained.

When methacrylic acid is produced by vaporphase oxidation or oxidative dehydrogenation of methacrolein, isobutylaldehyde or isobutyric acid using the methacrylic acid production catalyst of this invention, there is no particular limitation on the apparatus and conditions in its practice. The reaction can be performed under conditions which are generally used for the production of methacrylic acid by vapor-phase catalytic oxidation or vapor-phase catalytic oxidative dehydrogenation reaction.

For example, a gaseous mixture composed of starting compounds such as 1 to 10% by volume of methacrolein, isobutylaldehyde or isobutyric acid, 1 to 10 times the volume of the starting material of molecular oxygen, and inert gases as diluents such as nitrogen, carbon dioxide gas and steam (The use of steam suppresses the formation of by-products and is advantageous for the increased yield of the desired product) may be brought into contact with the methacrylic acid production catalyst at a temperature of 200° to 400° C. under 1 to 10 atmospheres at a space velocity of 100 to 5,000 hr$^{-1}$ (STP).

When methacrolein is used as the starting compound, methacrolein need not be always pure, and a methacrolein-containing gas obtained by catalytically reacting isobutylene or tertiary butanol may be used. The use of such a methacrolein-containing gas is especially recommended in an industrial process. Since the methacrylic acid production catalyst of this invention is formed by depositing a catalytically active substance layer having a specified composition on an inert carrier by the baking deposition method, it has high activity and can produce methacrylic acid in high yields with high selectivity. In particular, by adjusting the specific surface area, the pore volume and the pore diameter distribution to the specified range simultaneously, methacrylic acid can be produced in a higher yield with high selectivity.

Since in the methacrylic acid production catalyst of this invention, the catalytically active substance layer is maintained in a thin layer, heat accumulation at the time of methacrylic acid forming reaction can be decreased. As a result, the consecutive reaction of the resulting methacrylic acid can be suppressed, and the degradation of the catalyst by thermal loading can be prevented.

Since in the methacrylic acid production catalyst of this invention, the catalytically active substance layer is formed by the baking deposition method, the layer is deposited firmly onto the inert carrier, and has high mechanical strength and excellent resistance to peeling. Thus, the catalyst of this invention is fully satisfactory for industrial practice.

The methacrylic acid production catalyst of this invention exhibits excellent peformances over a long period of time, and even after use for long periods of time, the same high yield and high selectivity of the same degree as at the initiation of the reaction can be obtained without much elevating the reaction temperature.

The catalyst of this invention can be produced by a simple method with high reproducibility. By this invention, a methacrylic acid production catalyst having a uniform catalytic performances can be produced. Because of its excellent reproducibility, the catalyst is industrially excellent.

By the following Examples, the present invention will be specifically illustrated.

The conversion, the selectivity and one-pass yield are defined as follows.

$$\text{Conversion (\%)} = \frac{\text{Moles of starting compounds reacted}}{\text{Moles of fed starting compounds}} \times 100$$

$$\text{Selectivity (\%)} = \frac{\text{Moles of methacrylic acid formed}}{\text{Moles of starting compound reacted}} \times 100$$

$$\text{One-pass yield (\%)} = \frac{\text{Moles of methacrylic acid formed}}{\text{Moles of fed starting compounds}} \times 100$$

EXAMPLE 1

To 40 liters of heated deionized water were added 8,830 g of ammonium paramolybdate and 531.4 g of ammonium metavanadate. The mixture was stirred to dissolve them in deionized water.

Arsenious acid (123.7 g) and 85% phosphoric acid (523.8 g) were added to the solution, and then a solution of 4 liters of nitric acid (specific gravitiy 1.38) and 812.3 g of cesium nitrate in 5 liter of deionized water was added. They were stirred with heating to form a slurry (to be referred to as a slurry (A).

1,600 ml of a ring-like carrier composed of silicon carbide (outside diameter 6.0 mm, inside diameter of through-hole 3.0 mm, length 5.0 mm) was put into a stainless steel drum having an inside capacity of 20 liters adapted to be externally heated, and preheated to 120°-200° C. While the drum was rotated, the slurry (A) was sprayed onto the carrier to form a deposited layer. The carrier having a deposited layer formed thereon was calcined at 400° C. for 3 hours under air flowing to form a catalytically active substance layer to obtain a catalyst (I-1).

The composition (excluding oxygen) of this catalyst was $Mo_{12}P_{1.09}V_{1.09}C_{1.0}As_{0.3}$. The amount of the catalytically active substance deposited (as oxides, the same hereinafter) was 20 g per 100 ml of the carrier.

EXAMPLE 2

A spherical carrier (diameter 6.0 mm) composed of silicon carbide was measured in an amount of 1,600 ml. By the same way as in Example 1, the slurry (A) was deposited on the spherical carrier by the baking deposition method to obtain a catalyst (I-2).

The composition of the catalytically active substance layer of this catalyst was the same as Example 1. The amount of the catalytically active substance deposited was 20 g per 100 ml of the carrier.

EXAMPLE 3

1,600 ml of a ring-like carrier composed of a porous silica-alumina having a specific surface area of 0.3 m$^2$/g was measured. As in Example 1, the slurry (A) was deposited by the baking deposition method to obtain a catalyst (I-3).

The composition of the catalytically active substance layer of this catalyst was the same as in Example 1. The amount of the catalytically active substance deposited was 20 g per 100 ml of the carrier.

EXAMPLE 4

A spherical carrier (diameter 6.0 mm) composed of porous silica-alumina having a specific surface area of 0.3 m$^2$/g was measured to an amount of 1,600 ml, and the slurry (A) was deposited as in Example 1 by the baking deposition method to obtain a catalyst (I-4).

The composition of the catalytically active substance layer of this catalyst was the same as in Example 1, and the amount of the catalytically active substance was 20 g per 100 ml of the carrier.

EXAMPLE 5

Porous alpha-alumina ring-like carrier (outside diameter 6.0 mm; (through-hole) inside diameter 3.0 mm;

length 5.0 mm) having a specific surface area of 0.3 m²/g was measured to an amount of 1,600 ml, and by the baking deposition method as in Example 1, the slurry (A) was deposited on it to obtain a catalyst (I-5).

The composition of the catalytically active substance layer of this catalyst was the same as in Example 1. The amount of the catalytically active substance deposited was 20 g per 100 ml of the carrier.

EXAMPLE 6

A porous alpha-alumina spherical carrier having a specific surface area of 0.3 m²/g was measured to an amount of 1,600 ml, and in the same way as in Example 1, the slurry (A) was deposited on it by the baking deposition method to obtain a catalyst (I-6).

The composition of the catalytically active substance layer of this catalyst was the same as in Example 1, and the amount of the catalytically active substance deposited was 20 g per 100 ml of the carrier.

COMPARATIVE EXAMPLE 1

A ring-like carrier (outside diameter 6.0 mm, through-hole inside diameter 3.0 mm, length 5.0 mm) composed of the same silicon carbide as used in Example was measured in an amount of 1,600 ml, and immersed in a predetermined amount of the slurry (A). Then, the slurry was heated, and concentrated to dryness in an effort to deposit it on the carrier. But the deposited layer exfoliated successively, and a catalyst could not be obtained.

COMPARATIVE EXAMPLE 2

A spherical carrier (diameter 6.0 mm) composed of the same silicon carbide as used in Example 2 was measured to an amount of 1,600 ml, and as in Comparative Example 1, was immersed in a predetermined amount of the slurry (A). The slurry (A) was heated, concentrated to dryness in an attempt to deposit the slurry (A). The deposited layer was defoliated successively from the carrier, and a catalyst could not be obtained.

COMPARATIVE EXAMPLE 3

The same ring-like carrier (outside diameter 6.0 mm, through-hole inside diameter 3.0 mm, length 5.0 mm composed of the same porous silica-alumina as used in Example 5 was measured to an amount of 1,600 ml, and immersed in a predetermined amount of the slurry (A). The slurry (A) was heated, and concentrated to dryness to deposit the slurry (A) on the carrier. Simultaneously, the slurry was calcined as in Example 1 to obtain a catalyst (I-7).

The composition of the catalytically active substance layer of this catalyst was the same as in Example 1, and the amount of the catalytically active substance deposited was 20 g per 100 ml of the carrier.

COMPARATIVE EXAMPLE 4

A spherical carrier (diameter 6.0 mm) composed of the same porous silica-alumina as used in Example 4 was measured to an amount of 1,600 ml, and the slurry (A) was deposited in the same way as Comparative Example 3, and calcined to form a catalyst (I-8).

The composition of the catalytically active substance layer of this catalyst was the same as in Example 1, and the amount of the catalytically active substance deposited was 20 g per 100 ml of the carrier.

COMPARATIVE EXAMPLE 5

A ring-like carrier (outside diameter 6.0 mm; (through-hole) inside diameter 3.0 mm; length 5.0 mm) composed of the same porous alpha-alumina as used in Example 5 was measured to an amount of 1,600 ml. The slurry (A) was deposited on the carrier in the same way as in Comparative Example 3 to obtain a catalyst (I-9).

The composition of the catalytically active substance layer of this catalyst was the same as in Example 1, and the amount of the oxides of the catalytically active components was 20 g per 100 ml of the carrier.

COMPARATIVE EXAMPLE 6

The same porous alpha-alumina spherical carrier (diameter 6.0 mm) as used in Example 6 was measured in an amount of 1,600 ml, and in the same way as in Comparative Example 3, the slurry (A) was deposited on the carrier to obtain a catalyst (I-10).

The composition of the catalytically active component of this catalyst was the same as in Example 1, and the amount of the oxides of the catalytically active component deposited was 20 g per 100 ml of the carrier.

EXAMPLE 7

1,500 ml each of the catalysts (I-1) to (I-10) obtained in Examples 1 to 6 and Comparative Examples 3 to 6 was filled in a steel reactor. In this reactor, a gaseous mixture having the following average composition obtained by catalytically oxidizing isobutylene at 340° C. in the presence of a molybdenum-cobalt-tungsten-iron oxide multicomponent catalyst was introduced and oxidized at a space velocity of 1,200 hr$^{-1}$.

| Average composition of the gaseous mixture (% by volume) | |
| --- | --- |
| Methacrolein | 3.5 |
| isobutylene | 0.04 |
| Methacrylic acid + acetic acid | 0.24 |
| Steam | 20 |
| Oxygen | 9.0 |
| Others (inert gas composed mainly of nitrogen and carbon dioxide gas) | 67.2 |

The results are shown in Table 1.

The following can be understood from the results of Table 1.

When an inert carrier such as silicon carbide is used, the catalyst cannot be prepared by the immersion deposition method because the catalyst layer depositied dropped off from the carrier, but only by the baking deposition method, the catalyst could be prepared.

With a porous inert carrier, a catalyst can be prepared by the immersion deposition method. But the catalyst obtained by the immersion deposition method gives both inferior methacrylic acid selectivity and one-pass yield as compared with the catalyst of this invention obtained by the baking deposition method.

TABLE 1

| | Carrier | | | Method of catalyst preparation *2 | Specific surface area (m²/g) | Pore volume (ml/g) | Pore diameter distribution | | | Reaction temperature (°C.) | Methacrolein conversion (mole %) | Methacrolein acid selectivity (mole %) | One-pass yield (mole %) |
|---|---|---|---|---|---|---|---|---|---|---|---|---|---|
| | Type | Particle diameter (mm) *1 | Shape | | | | A | B | C | | | | |
| Example | | | | | | | | | | | | | |
| 1 | SiC | 6 × 3 × 5 | ring | baking *4 | 7.4 | 0.354 | 43 | 5 | 50 | 300 | 89.2 | 87.1 | 77.7 |
| 2 | " | 6 | sphere | " | 7.2 | 0.357 | 42 | 8 | 48 | 300 | 88.1 | 86.8 | 76.5 |
| 3 | SiO₂—Al₂O₃ | 6 × 3 × 5 | ring | " | 7.4 | 0.412 | 30 | 13 | 54 | 300 | 90.1 | 86.3 | 77.8 |
| 4 | " | 6 | sphere | " | 7.0 | 0.419 | 32 | 12 | 53 | 300 | 88.7 | 86.1 | 76.4 |
| 5 | α-Al₂O₃ | 6 × 3 × 5 | ring | " | 9.2 | 0.288 | 31 | 7 | 60 | 300 | 89.8 | 86.4 | 77.6 |
| 6 | " | 6 | sphere | " | 8.6 | 0.297 | 41 | 3 | 54 | 300 | 88.3 | 85.9 | 75.8 |
| Comparative Example | | | | | | | | | | | | | |
| 1 | SiC | 6 × 3 × 5 | ring | immersion *5 | *3 | | | | | | | | |
| 2 | " | 6 | sphere | immersion *5 | *3 | | | | | | | | |
| 3 | SiO₂—Al₂O₃ | 6 × 3 × 5 | ring | immersion *5 | 6.0 | 0.584 | 3 | 39 | 54 | 300 | 86.9 | 84.5 | 73.4 |
| 4 | " | 6 | sphere | immersion *5 | 5.5 | 0.576 | 3 | 44 | 49 | 300 | 86.0 | 84.2 | 72.4 |
| 5 | α-Al₂O₃ | 6 × 3 × 5 | ring | immersion *5 | 5.8 | 0.608 | 70 | 23 | 5 | 300 | 88.8 | 84.7 | 75.2 |
| 6 | " | 6 | sphere | immersion *5 | 5.2 | 0.504 | 73 | 20 | 4 | 300 | 88.2 | 84.3 | 74.4 |

*1 Ring = outside diameter × through-hole inside diameter × length; Sphere = diameter
*2 A: Proportion of pores with a diameter in the range of 1-10 micrometer based on the total pore volume (%) B: Proportion of pores with a diameter of 0.5 to less than 1 micrometer based on the total pore volume (%) C: Proportion of pores with a diameter of 0.1 to less than 0.5 micrometer based on the total pore volume (%)
*3 The catalyst could not be prepared
*4 Baking deposition method
*5 Immersion deposition method

EXAMPLE 8

The same slurry (A) as prepared in Example 1 was divided into two equal portions. Using one portion of the slurry (A), four batches of catalysts (II-1) to (II-4) were prepared. Likewise, by using the other portion (A), four batches of catalysts (II-5) to (II-8) were prepared by the immersion deposition method as in Comparative Example 3.

In catalysts (II-1) to (II-8), the amount of the catalytically active substance deposited was 20 g per 100 ml of the carrier.

By using each of the catalysts (II-1) to (II-8), the same oxidation reaction was carried out as in Example 7.

The results are shown in Table 2.

and the catalysts were high in activity, and the deviations of the activity were small. Namely, according to the baking deposition method, catalysts could be prepared with good reproducibility.

In contrast, catalysts prepared by the immersion deposition method, the deviations of physical property values are great, and therefore, their catalyst performances varied greatly.

EXAMPLE 9

Ammonium molybdate (4,770 g) was dissolved in 18 liters of water.

Separately, 259.6 g of 85% ortho-phosphoric acid was diluted with 1,350 ml of water, and 163.3 g of cupric nitrate and 111.4 g of arsenious acid were dissolved

TABLE 2

| Catalyst | Catalyst preparation method | Batch No. | Specific surface (m²/g) | Pore volume (ml/g) | Pore diameter distribution *2 | | | Reaction temperature (°C.) | Methacrolein conversion (mole %) | Methacrolein acid selectivity (mole %) | One-pass yield (mole %) |
|---|---|---|---|---|---|---|---|---|---|---|---|
| | | | | | A | B | C | | | | |
| II-1 | baking *4 | 1 | 7.2 | 0.413 | 31 | 13 | 54 | 300 | 90.0 | 86.5 | 77.9 |
| II-2 | " | 2 | 7.0 | 0.410 | 31 | 11 | 55 | 300 | 89.9 | 86.3 | 77.6 |
| II-3 | " | 3 | 7.3 | 0.416 | 33 | 12 | 52 | 300 | 90.3 | 86.3 | 77.9 |
| II-4 | " | 4 | 6.9 | 0.419 | 32 | 14 | 51 | 300 | 89.5 | 86.0 | 77.0 |
| II-5 | immersion *5 | 1 | 7.0 | 0.603 | 3 | 35 | 59 | 300 | 89.4 | 83.3 | 74.8 |
| II-6 | immersion *5 | 2 | 6.5 | 0.551 | 4 | 47 | 47 | 300 | 87.0 | 84.3 | 73.3 |
| II-7 | immersion *5 | 3 | 6.9 | 0.600 | 3 | 41 | 53 | 300 | 89.8 | 83.5 | 75.0 |
| II-8 | immersion *5 | 4 | 6.2 | 0.513 | 6 | 44 | 47 | 300 | 85.8 | 84.0 | 72.1 |

*2, *4, *5: Same as the footnotes in Table 1.

From Table 2, the following can be understood.

The catalysts prepared by the baking deposition method, the deviations of the specific surface area, pore volume and pore size diameter distribution were small, in the dilution, and they were added to the above aqueous solution of ammonium molybdate. With heating, the mixture was thoroughly stirred and aged.

Separately 259.6 g of 85% ortho-phosphoric acid was diluted with 1,350 ml of water, and 204.8 g of vanadium pentoxide was added. When water was evaporated while the mixture was heated and stirred, a yellow complex was obtained. The complex was added to the reaction precipitate of phosphorus, molybdenum, copper and arsenic. Finally, a solution of 126.3 of potassium hydroxide in 1,350 ml of water was added to prepare a slurry (B).

By using this slurry (B), it was deposited and baked as in Example 5, a catalyst (III-1) was prepared.

The composition of the catalytically active substance layer was as follows in terms of atomic ratio.

$$Mo_{12}P_2Cu_{0.3}K_1V_1As_{0.5}.$$

The amount of the catalytically active substance was 20 g per 100 ml of the carrier.

COMPARATIVE EXAMPLE 7

By using the slurry (B), a catalyst (III-2) was prepared in the same way as in Comparative Example 5.

The amount of the catalytically active substance in the catalyst (III-2) was 20 g per 100 ml of the carrier.

EXAMPLE 10

85% phosphoric acid (553.8 g) was added to an aqueous solution of 5,088 g of ammonium molybdate in 10 liters of deionized water, and then an aqueous solution of 936.2 g of cesium nitrate in 3.6 liters of water was added. Furthermore, 582.6 g of bismuth nitrate and 194.3 g of antimony pentoxide were added as a powder. Finally, an aqueous solution of 120.1 g of chromic anhydride and 138.2 g of selenium dioxide in 3.6 liters of water was added to obtain a slurry (C).

Using this slurry (C), baking deposition was carried out in the same way as in Example 2 to give a catalyst (IV-I).

The composition of the catalytically active substance layer of this catalyst was as follows in atomic ratio $$Mo_{12}P_2Bi_{0.5}Sb_{0.5}Cs_{2.0}Cr_{0.5}Se_{0.5}.$$

The amount of the catalyst component substances deposited was 20 g per 100 ml of the carrier.

COMPARATIVE EXAMPLE 8

By using the slurry (C), a catalyst was prepared by the immersion deposition method in the same way as Comparative Example 2. The deposition layer dropped off one after another from the carrier, and a catalyst could not be obtained.

EXAMPLE 11

Molybdenum trioxide (4,802 g), 252.8 g of vanadium pentoxide, 44.2 g of copper oxide, 44.4 g of iron oxide, 41.9 g of tin oxide and 320.5 g of orthophosphoric acid (85%) were dispersed in 40 l of deionized water. The dispersion was heated with stirring for about 3 hours, and then 15.6 g of potassium hydroxide was added. Furthermore, the mixture was refluxed with boiling for about 3 hours to obtain a slurry (D).

By using this slurry (D), a catalyst (V-1) was obtained in the same way as in Example 1 by baking deposition.

The composition of the catalytically active substance layer of this catalyst (V-1) was as follows in atomic ratio.

$$Mo_{12}P_1V_1K_{0.1}Cu_{0.2}Fe_{0.2}Sn_{0.1}.$$

The amount of the catalytically active substances deposited was 20 g per 100 ml of the carrier.

COMPARATIVE EXAMPLE 9

By using the slurry (D), a catalyst was prepared by the same immersion deposition method as in Comparative Example 1. But the deposition layer dropped off one after another, and a catalyst could not be obtained.

EXAMPLE 12

In Example 1, the scale of catalyst preparation was decreased to half, and 272.3 g of barium nitrate was used instead of cesium nitrate. Otherwise, in the same way as in Example 1 a slurry (E) was prepared.

By using the slurry (E), a catalyst (VI-1) was obtained by the baking deposition method as in Example 6.

The composition of the catalytically active substance layer of this catalyst was as follows in atomic ratio.

$$Mo_{12}P_{1.09}As_{0.3}V_{1.09}Ba_{0.5}.$$

The amount of the catalytically active substances deposited was 20 g per 100 ml of the carrier.

COMPARATIVE EXAMPLE 10

Using the slurry (E), a catalyst (VI-2) was prepared by the immersion deposition method in the same way as in Comparative Example 6.

The composition of the catalytically active substances of this catalyst (VI-2) was the same as in Example 12, and the amount of the catalytically active substances depositied was 20 g per 100 ml of the carrier.

EXAMPLE 13

In Example 1, together with 812.3 g of cesium nitrate, 130.7 g of germanium oxide, 222.7 g of zirconium nitrate and 121.3 g of cobalt nitrate were added, and otherwise, a slurry (F) was prepared as in Example 1.

Using this slurry (F), a catalyst (VII-1) was prepared by the baking deposition method in the same way as in Example 5.

The composition of the catalytically active substance layer of the catalyst (VII-1) was as follows in aromatic ratio.

$$Mo_{12}P_{1.09}As_{0.3}V_{1.09}Cs_{1.0}Ge_{0.3}Zr_{0.2}Co_{0.1}.$$

The amount of the catalytically active substances deposited was 20 g per 100 ml of the carrier.

COMPARATIVE EXAMPLE 11

Using the slurry (F), a catalyst (VII-2) was prepared by the same immersion deposition method as in Comparative Example 5.

The composition of the catalytically active substances of the catalyst (VII-2) was the same as in Example 13, and the amount of the catalytically active substances deposited was 20 g per 100 ml of the carrier.

EXAMPLE 14

In Example 1, 199.5 g of tellurium dioxide, 239.2 g of manganese nitrate and 242.3 g of nickel nitrate were added together with 812.3 g of cesium nitrate. Otherwise, as in Example 1, a slurry (G) was prepared.

By using this slurry (G), a catalyst (VIII-1) was obtained by the same baking deposition method as in Example 4.

The composition of the catalytically active substance layer of this catalyst (VIII-1) was as follows in atomic ratio.

$Mo_{12}P_{1.09}As_{0.3}V_{1.09}Cs_{1.0}Te_{0.3}Mn_{0.2}Ni_{0.2}$.

The amount of the catalytically active substances was 20 g per 100 ml of the carrier.

COMPARATIVE EXAMPLE 12

By using the slurry (G), a catalyst (VIII-2) was prepared by the same immersion deposition method as in Comparative Example 4.

The amount of the catalytically active substances of the catalyst (VIII-2) deposited was 20 g per 100 ml of the carrier.

EXAMPLE 15

In Example 1, 562.8 g of ammonium tungsten, 247.9 g of zinc nitrate and 70.8 g of silver nitrate were added together with 812.3 g of cesium nitrate. Otherwise, in the same way as in Example 1, a slurry (H) was prepared.

By using the slurry (H), a catalyst (IX-1) was prepared by the same baking deposition method as in Example 5.

The composition of the catalytically active substance layer of this catalyst (IX-1) was as follows in atomic ratio.

$Mo_{12}P_{1.09}As_{0.3}V_{1.09}Cs_{1.0}W_{0.5}Zn_{0.2}Ag_{0.1}$

The amount of the catalytically active substances deposited was 20 g per 100 ml of the carrier.

COMPARATIVE EXAMPLE 13

By using the slurry (H), a catalytic (IX-2) was prepared as in Comparative Example 3.

The amount of the catalytically active substances of this catalyst (IX-2) deposited was 20 g per 100 ml of the catalyst.

EXAMPLE 16

In Example 1, 555.0 g of thallium nitrate, 166.1 g of niobium pentoxide, 441.0 g of strontium nitrate, and 96.0 g of palladium nitrate were added together with 812.3 g of cesium nitrate, otherwise, in the same way as in Example 1, a slurry (I) was prepared as in Example 1.

By using this slurry (I), a catalyst (X-1) was prepared by baking deposition in the same way as in Example 2.

The composition of the catalytically active substance layer. The layer of this layer of the catalyst (X-1) is as follows in atomic ratios.

$Mo_{12}P_{1.09}As_{0.3}V_{1.09}Cs_{1.0}Tl_{0.5}Sr_{0.5}Nb_{0.3}Pd_{0.1}$

The amount of the catalytically active substance was 20 g per 100 ml of the carrier.

COMPARATIVE EXAMPLE 14

By using the slurry (I), catalyst preparation was attempted by immersion deposition as in Comparative Example 2. However, the deposited layers dropped off one after another, and a catalyst could not be obtained.

EXAMPLE 17

In Example 1, 307.2 g of rubidium nitrate, 196.8 g of calcium nitrate and 135.4 g of rhodium nitrate were added together with 812.3 g of cesium nitrate. Otherwise, in the same way as in Example 1, the slurry (J) was obtained. By using the slurry (J), baking deposition was carried out in the same way as in Example 1, and a catalyst (XI-1) was prepared.

The composition of the catalytically active substance layer as in the catalyst (XI-1) was as follows in atomic ratios.

$Mo_{12}P_{1.09}As_{0.3}V_{1.09}Cs_{1.0}Rb_{0.5}Ca_{0.2}Rh_{0.1}$

The amount of the catalytically active layers deposited was 20 g per 100 ml of the carrier.

COMPARATIVE EXAMPLE 15

By using a slurry (J), immersion deposition was attempted in the same way as in Comparative Example 1. But the deposition layers dropped off one after another, and a catalyst could not be obtained.

EXAMPLE 18

Molybdenum trioxide (4,320 g), 227.4 of vanadium pentoxide and 432.5 g of 85% of ortho-phosphoric acid were added to 15 liters of water and the mixture was refluxed under heating for 24 hours. Cerium oxide (215.1 g), 379.2 g of potassium nitrate, and 39.8 g of (powdery) copper oxide were added to prepare a slurry (K).

By using this slurry (K), baking deposition was carried out as in Example 6 to obtain a catalyst (XII-1).

The composition of the catalytically active substance layer of this catalyst was as follows in atomic ratio.

$Mo_{12}V_1P_{1.5}K_{1.5}Cu_{0.2}Ce_{0.5}$

The amount of the catalytically active substances deposited was 20 g per 100 mg of the carrier.

COMPARATIVE EXAMPLE 16

By using the slurry (K), a catalyst (XII-2) was obtained.

The composition of the catalytically active substance layer of this catalyst was the same as in Example 18, and the amount of the catalytically active substances deposited was 20 g per 100 ml of the carrier.

EXAMPLE 19

By using each of the catalysts obtained in Examples 9 to 18 and Comparative Examples 7 to 16, the same oxidation reaction as in Example 7 was carried out.

The results are shown in Table 3.

TABLE 3

| | Type of the catalyst | Type(shape) of the carrier | Catalyst preparing method | Specific surface area (m²/g) | Pore volume (ml/g) | Pore diameter distribution *2 | | | Reaction temperature (°C.) | Methacrolein conversion (mole %) | Methacrylic selectivity (mole %) | One-pass yield (mole %) |
| --- | --- | --- | --- | --- | --- | --- | --- | --- | --- | --- | --- | --- |
| | | | | | | A | B | C | | | | |
| Ex. 9 | III-1 | α-Al₂O₃ | baking *4 | 8.4 | 0.278 | 33 | 5 | 60 | 310 | 87.5 | 84.0 | 73.5 |

TABLE 3-continued

| | Type of the catalyst | Type(shape) of the carrier | Catalyst preparing method | Specific surface area (m²/g) | Pore volume (ml/g) | Pore diameter distribution *2 A | B | C | Reaction temperature (°C.) | Methacrolein conversion (mole %) | Methacrylic selectivity (mole %) | One-pass yield (mole %) |
|---|---|---|---|---|---|---|---|---|---|---|---|---|
| CEx. 7 | III-2 | α-Al₂O₃ (ring) | immersion *5 | 5.1 | 0.575 | 65 | 29 | 4 | 310 | 86.7 | 82.5 | 71.5 |
| Ex. 10 | IV-1 | SiC (sphere) | baking | 5.9 | 0.290 | 36 | 12 | 50 | 310 | 84.3 | 80.9 | 68.2 |
| CEx. 8 | IV-2 | SiC (sphere) | immersion | *3 | | | | | | | | |
| Ex. 11 | V-1 | SiC (ring) | baking | 7.3 | 0.310 | 46 | 3 | 48 | 320 | 85.9 | 79.5 | 68.3 |
| CEx. 9 | V-2 | SiC (ring) | immersion | *3 | | | | | | | | |
| Ex. 12 | VI-1 | α-Al₂O₃ (sphere) | baking | 9.7 | 0.320 | 40 | 8 | 49 | 300 | 89.3 | 86.6 | 77.3 |
| CEx. 10 | VI-2 | α-Al₂O₃ (sphere) | immersion | 5.3 | 0.550 | 68 | 25 | 4 | 300 | 89.3 | 85.0 | 75.9 |
| Ex. 13 | VII-1 | α-Al₂O₃ (ring) | baking | 8.0 | 0.281 | 36 | 6 | 54 | 300 | 88.5 | 81.9 | 72.5 |
| CEx. 11 | VII-2 | α-Al₂O₃ (ring) | immersion | 5.0 | 0.613 | 62 | 27 | 7 | 300 | 87.4 | 79.6 | 69.6 |
| Ex. 14 | VIII-1 | SiO₂—Al₂O₃ (sphere) | baking | 6.5 | 0.414 | 31 | 11 | 55 | 300 | 86.0 | 85.7 | 73.7 |
| CEx. 12 | VIII-2 | SiO₂—Al₂O₃ (sphere) | immersion | 5.0 | 0.574 | 8 | 40 | 48 | 300 | 82.7 | 83.8 | 69.3 |
| Ex. 15 | IX-1 | SiO₂—Al₂O₃ (ring) | baking *4 | 7.1 | 0.381 | 34 | 13 | 50 | 300 | 87.5 | 85.5 | 74.8 |
| CEx. 13 | IX-2 | SiO₂—Al₂O₃ (ring) | immersion *5 | 5.5 | 0.533 | 4 | 43 | 50 | 300 | 84.1 | 83.5 | 70.2 |
| Ex. 16 | X-1 | SiC (sphere) | baking | 6.6 | 0.312 | 40 | 10 | 47 | 310 | 85.2 | 81.5 | 69.4 |
| CEx. 14 | X-2 | SiC (sphere) | immersion | *3 | | | | | | | | |
| Ex. 17 | XI-1 | SiC (ring) | baking | 7.6 | 0.339 | 39 | 7 | 51 | 310 | 85.3 | 81.6 | 69.6 |
| CEx. 15 | XI-2 | SiC (ring) | immersion | *3 | | | | | | | | |
| Ex. 18 | XII-1 | α-Al₂O₃ (sphere) | baking | 8.4 | 0.291 | 42 | 5 | 50 | 290 | 92.7 | 81.1 | 75.2 |
| CEx. 16 | XII-2 | α-Al₂O₃ (sphere) | immersion | 5.0 | 0.493 | 70 | 23 | 3 | 290 | 92.3 | 79.2 | 73.1 |

*2, *3, *4, *5: Same as footnotes to Table 1.
Ex. = Example
CEx. = Comparative Example

EXAMPLE 20

By using the catalyst (I-3) obtained in Example 3, the continuous reaction was carried out for 4,000 hours under the same conditions as in Example 7. The initial reaction temperature was adjusted to 300° C. To obtain almost the same methacrolein conversion as at the initiation of the reaction after 4,000 hours, it was sufficient to raise the temperature by 6° C. The reaction results after about 4,000 hours were as follows;

Reaction temperature: 306° C.; Methacrolein conversion: 88.7%; methacrylic acid selectivity: 86.7%.

EXAMPLE 21

By using the catalyst (I-3) obtained in Example 3, isobutylaldehyde was oxidatively dehydrogenated. Specifically, 1,500 ml of the catalyst (I-3) was filled in a steel reaction tube having a diameter of 25.4 mm, and a gaseous mixture of isobutylaldehyde, oxygen, steam and nitrogen in a volume ratio of 5.0:12.5:10.0:72.5 was introduced at a space velocity of 800 hr⁻¹, and the reaction was carried out at a temperature of 290° C.

The results are shown in Table 4.

COMPARATIVE EXAMPLE 17

In Example 21, the catalyst (I-7) obtained in Comparative Example 3 was used instead of the catalyst (I-3). Otherwise, in the same way as in Example 21, isobutylaldehyde was oxidatively dehydrogenated.

The results are shown in Table 4.

EXAMPLE 22

By using the catalyst (I-3) obtained in Example 3, isobutyric acid was oxidatively dehydrogenated.

Specifically, 1,500 ml of the catalyst (I-3) was filled in a steel reactor having a diameter of 25.4 mm, and a gaseous mixture composed of isobutyric acid:oxygen:-steam:nitrogen=5.0:10.0:10.0:75.0 (volume ratios) was introduced at a space velocity of 2.000 hr⁻¹ and reacted at 290° C.

The results are shown in Table 5.

COMPARATIVE EXAMPLE 18

In Example 22, the catalyst (I-7) obtained in Comparative Example 3 was used instead of the catalyst (I-3). Otherwise in the same way as in Example 22, isobutyric acid was oxidatively dehydrogenated.

The results are shown in Table 5.

TABLE 4

| | Reaction temperature (°C.) | isobutylaldehyde conversion (mole %) | Selectivity (mole %) | | One-pass yield (mole %) | |
|---|---|---|---|---|---|---|
| | | | Methacrylic acid | Methacrolein | Methacrylic acid | Methacrolein |
| Ex. 21 | 290 | 100 | 68.0 | 14.5 | 68.0 | 14.5 |
| CEx. 17 | 290 | 100 | 66.8 | 13.9 | 66.8 | 13.9 |

TABLE 5

| | Reaction temperature (°C.) | isobutylaldehyde conversion (mole %) | Selectivity (mole %) | One-pass yield (mole %) |
|---|---|---|---|---|
| Ex. 22 | 290 | 99.5 | 80.5 | 80.1 |
| CEx. 18 | 290 | 98.7 | 78.2 | 77.2 |

EXAMPLE 23

8,830 g of ammonium paramolybdate and 531.4 g of ammonium metavanadate were added to 40 liters of heated deionized water, and the mixture was stirred to form a solution.

Arsenious acid (123.7 g) and 523.8 g of phosphoric acid (85% by weight) were taken into the solution. Then, 4 liters of nitric acid (specific gravity 1.38) and 812.3 g of cesium nitrate were added to 5 liters of deionized water. The mixture was heated and stirred to prepare a slurry (a).

In the above slurry (a), the amount of phosphoric acid was changed to 624.7 g and otherwise, a slurry (b) was prepared in the same way as above. 1,600 ml of a pelletized carrier (outside diameter 6 mm and a length of 6.0 mm) composed of silicon carbide was put in a stainless steel drum having an inside capacity of 20 liters and could be heated externally. It was pre-heated to 120° to 200° C. While the drum was rotated, the slurry (a) and then the slurry (b) were successively sprayed onto the carrier to form a deposited layer.

The carrier having this deposited layer formed was calcined for 3 hours at 400° C. under an air current to form a catalytically active substance layer to obtain a catalyst (1). The amount of the catalytically active substances of the catalyst (1) deposited (as oxides; same hereinafter) was 20 g per 100 ml of the carrier. After the drying and calcining of the slurry (a), the composition of the oxides (atomic ratio excluding oxygen; the same hereinafter) was as follows:

$Mo_{12}P_{1.09}V_{1.09}Cs_{1.0}As_{0.3}$

After the drying and calcination of the slurry (b), the composition of the oxides was as follows:

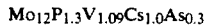

$Mo_{12}P_{1.3}V_{1.09}Cs_{1.0}As_{0.3}$

The catalyst (1) in an amount of 1,500 ml was filled in a steel reactor having an inner diameter of 25.4 mm, and isobutylene was catalytically oxidized in the vapor phase in the presence of a Mo-Co-W-Fe oxide-type multi-component catalyst and the resulting gaseous mixture having the following composition was introduced, and oxidized at a reaction temperature of 300° C. and a space velocity of 1,200 hr$^{-1}$ (STP). The results are Table 6.

| Composition of the gaseous mixture subjected to oxidation | |
|---|---|
| Methacrolein | 3.5 (vol %) |
| isobutylene | 0.04 |
| Methacrylic acid + acetic acid | 0.24 |
| Steam | 20 |
| Oxygen | 9 |
| Others (mainly nitrogen) | 67.22 |

EXAMPLE 24

The proportions of isobutylene and the other component (mainly nitrogen) in the gaseous mixture to be subjected to the oxidation reaction were changed to 0.08% by volume and 67.18% by volume. Otherwise, the oxidation reaction was carried out in the same way as in Example 23. The results are shown in Table 6.

Example 24 was carried out in order to examine the influence of the catalyst used in the later-stage reaction of the unreacted isobutuylene. As compared with Example 23, the gaseous mixture having an increased unreacted isobutylene content in the pre-stage reaction outlet gas was used.

With the catalyst (1), even when the amount of isobutylene in the methacrolein-containing gaseous mixture was increased, the decrease in activity was relatively small. From this result, it is understood that the catalyst (1) was very stable to changes to the reaction conditions in the pre-stage reaction in the continuous process and is suitable as a commercial catalyst.

EXAMPLE 25

In Example 23, a catalyst (2) was prepared in the same way as in Example 23 except that instead of the pelletized carrier, 1,600 ml of a ring-like carrier having an outside diameter of 6 mm, a length of 5 mm, and a through-hole inside diameter of 3 mm was used.

The composition of the catalytically active substance layer of this catalyst (2) was the same as in Example 23, and the amount of the catalytically active substances was 20 g per 100 ml of the carrier.

In the following, the catalyst (2) was used instead of the catalyst (1). The same starting gas as having the following average gas composition was used. Otherwise, the oxidation reaction was carried out as in Example 24. The results are shown in Table 6.

| Methacrolein | 3.5 (% by volume) |
|---|---|
| isobutylene | 0.08 |
| Methacrylic acid + acetic acid | 0.24 |
| Steam | 20 |
| Oxygen | 9 |
| Others (mainly nitrogen) | 67.18 |

From the results of Example 25, when the shape of the carrier was changed from a pellet to a ring-like shape, it can be understood that when a double deposited layer as in the catalyst (2) is used, the decrease in activity by the remaining isobutylene is considerably suppressed.

EXAMPLE 26

Ammonium molybdate (4,770) was dissolved in 18 litters of water.

Separately, 259.6g of 85% ortho-phosphoric acid was diluted with 1,350 ml of water, and 204.8 g of vanadium pentoxide was added. With heating and stirring, water was evaporated t obtain a yellow complex. This complex was added to the reaction precipitate of the phosphorus, molybdenum, copper and arsenic. Finally, a solution of 126.3 g of potassium hydroxide in 1,350 ml of water to prepare a slurry (c).

In the preparation of the slurry (c), the amounts of copper nitrate and potassium hydroxide used were changed to 54.4 g and 189.5 g, respectively. Otherwise by the same method as above to prepare a slurry (d).

In Example 23, a ring-like carrier composed of alpha-alumina (having an outside diameter of 6 mm, a length 4 mm and an inside diameter of 3 mm) was used instead of the pelletized carrier. First the slurry (c) and then the slurry (d) were successively deposited. Otherwise, in the amount of the catalytically active substances deposited in the catalyst (3) was 20 g per 100 ml of the carrier.

After drying and calcination of the slurry (c), the composition of the oxides was as follows:

$Mo_{12}P_2Cu_{0.3}K_1V_1As_{0.5}$

After drying and calcination of the slurry (d), the composition of the oxides was as follows:

$Mo_{12}P_2Cu_{0.1}K_{1.5}V_1As_{0.5}$

Instead of the catalyst (2), the catalyst (3) was used, and the oxidation reaction was carried out in the same way as in Example 25. The results are shown in Table 7.

EXAMPLE 27

85% phosphoric acid (553.8 g) was added to an aqueous solution of 5,088 g of ammonium molybdate in 10 liters of deionized water, and an aqueous solution of 936.2 g of cesium nitrate in 3.6 liters of water was added. Furthermore, 582.6 g of bismuth nitrate and 194.3 g of antimony pentoxide both as a powder were added. Finally an aqueous solution of 120.1 g of chromic anhydride and 133.2 g of selenium dioxide in 3.6 liters of water was added to obtain a slurry (e). In the preparation of the slurry (e), the amount of antimony pentoxide was changed to 19.4 g. Otherwise in the same way as above, a slurry (f) was prepared as above.

In Example 23, a spherical carrier having an outside diameter of 6 mm composed of silicon carbide was used instead of the pelletized carrier, and the slurry (e) and then the slurry (f) were successively baked and deposited. Otherwise in the same way as in Example 23, a catalyst (4) was prepared.

The amount of the catalytically active substance layer deposited in the catalyst (4) was 20 g per 100 ml of the carrier. After the drying and calcination of the slurry (e), the composition of the oxides was as follows:

$Mo_{12}P_2Bi_{0.5}Sb_{0.5}Cs_{2.0}Cr_{0.5}Se_{0.5}$

After drying and calcination of the slurry (f), the composition of the oxides was as follows:

Subsequently, in the same way as in Example 25, the oxidation reaction was carried out by using the catalyst (4) instead of the catalyst (2).

The results are shown in Table 7.

EXAMPLE 28

Molybdenum trioxide (4,802 g), 252.8 g of vanadium pentoxide, 44.2 g of copper oxide, 44.4 g of iron oxide, 41.9 g of tin oxide and 320.5 g of 85% ortho-phosphoric acid were dispersed in 40 liters t of deionized water. The dispersion was stirred with heating for about 3 hours, and 15.6 g of potassium hydroxide was added. Further, the mixture was refluxed with boiling for 3 hours to prepare a slurry (g).

In the preparation of the slurry (g), the amount of vanadium pentoxide and ortho-phosphoric acid used were changed to 303.4 g and 384.6 g. Otherwise, a slurry (h) was prepared.

Then, in Example 23, a ring-like carrier (having an outside diameter of 6 mm, a length of 5 mm, and a through-hole inside diameter of 3 mm) composed of silicon carbide was used instead of the pelletized carrier. The slurry (g) and then the slurry (h) were successively deposited, and in the same way as in Example 23, a catalyst (5) was prepared.

The amount of the catalytically active substances in the catalyst (5) was 20 g per 100 ml of the carrier. After drying and calcination of the slurry (g), the composition of the oxides was as follows:

$Mo_{15}P_1V_1K_{0.1}Cu_{0.2}Fe_{0.2}Sn_{0.1}$

After drying and calcination of the slurry (h), the composition of the oxides was as follows:

$Mo_{12}P_{1.2}V_{1.2}K_{0.1}Cu_{0.2}Fe_{0.2}Sn_{0.1}$

Except that the catalyst (5) was used instead of the catalyst (2), the same oxidation reaction as in Example 25 was carried out. The results are shown in Table 7.

EXAMPLE 29

In the slurry (a) of Example 23, the catalyst preparation scale was decreased to half, and 272.3 g of barium nitrate was used instead of cesium nitrate. Otherwise, a slurry (i) was prepared in the same way as in Example 23.

In the preparation of the slurry (i), the amount of arsenic acid and barium nitrate were changed to 20.6 g and 435.7 g, respectively.

Then in Example 23, a pelletized carrier (having an outside diameter of 6 mm, a length of 6 mm) composed of alpha-alumina was used instead of the pelletized carrier composed of silicon carbide. First, the slurry (i) and then, the slurry (j) was successively depositied. Otherwise, in the same way as in Example 23, a catalyst (6) was prepared.

The amount of the catalytically active substances in the catalyst deposited was 20 g per 100 ml of the carrier. After drying and calcination of the slurry (i), the composition of the oxides was as follows:

$Mo_{12}P_{1.09}V_{1.09}Ba_{0.5}As_{0.3}$

After drying and calcination of the slurry (j), the composition of the oxides was as follows:

$Mo_{12}P_{1.09}V_{1.09}Ba_{0.8}As_{0.1}$

Subsequently, by using the catalyst (6) instead of the catalyst (2), and otherwise, an oxidation reaction was carried out as in Example 25.

The results are shown in Table 7.

EXAMPLE 30

In Example 23, together with 812.3 g of cesium nitrate, 130.7 g of germanium oxide, 222.7 g of zirconium nitrate and 121.3 g of cobalt nitrate were added. Otherwise, in the same way as in Example 23, a slurry (k) was prepared.

In the preparation of the slurry (k), the amount of cesium nitrate and zirconium nitrate were changed to 1,218.5 g and 334.1 g. Otherwise, in the same way as above, a slurry (l) was prepared.

Then in Example 23, a ring-like carrier composed of alpha-alumina (having an outside diameter of 6 mm, a length of 5 mm, and an inside diameter of 3 mm) was used instead of the pelletized carrier. An operation of first depositing the slurry (k) and then an operation of depositing a slurry (l) were each repeated twice. Otherwise, in the same way as in Example 23, a catalyst (7) was prepared.

The amount of the catalytically active substances in this catalyst (7) deposited was 20 g per 100 ml of the carrier. After drying and calcination of the slurry (k), the composition of the oxides was as follows:

$$Mo_{12}P_{1.09}As_{0.3}V_{1.09}Cs_{1.0}Ge_{0.3}Zr_{0.2}Co_{0.1}$$

After drying and calcination of the slurry (l), the composition of the oxides was as follows:

$$Mo_{12}P_{1.09}As_{0.3}V_{1.09}Cs_{1.5}Ge_{0.3}Zr_{0.3}Co_{0.1}$$

In the same way as in Example 25, the same oxidation reaction as in Example 25 was carried out except that the catalyst (7) was used instead of the catalyst (2).

The results are shown in Table 7.

EXAMPLE 31

In Example 23, 199.5 g of tellurium dioxide, 239.2 g of manganese nitrate and 242.3 g of nickel nitrate were added together with 812.3 g of cesium nitrate. Otherwise in the same way as in Example 23, a slurry (m) was prepared.

In the preparation of the slurry (m), the amounts of ammonium metavanadate, manganese nitrate and nickel nitrate deposited were changed to 633.8 g, 358.8 g and 363.5 g, respectively. Otherwise, in the same way, a slurry (n) was prepared.

Then, in Example 23, a pelletized carrier (having an outside diameter of 6 mm and a length of 6 mm) of silica-alumina was used instead of the pelletized carrier of silicon carbide. First, the slurry (m) and then the slurry (n) were successively deposited on the carrier twice. Otherwise, a catalyst (8) was prepared as in Example 23.

The amount of the catalytically active substances in the catalyst (8) was 20 g per 100 ml of the carrier. After the drying and calcination of the slurry (m), the composition of the oxides was as follows:

$$Mo_{12}P_{1.09}As_{0.3}V_{1.09}Cs_{1.0}Te_{0.3}Mn_{0.2}Ni_{0.2}$$

After the drying and calcination of the slurry (n), the composition of the oxides was as follows:

$$Mo_{12}P_{1.09}As_{0.3}V_{1.3}Cs_{1.0}Te_{0.3}Mn_{0.3}Ni_{0.3}$$

An oxidation reaction was carried out in the same way as in Example 25 except that the catalyst (8) was used instead of the catalyst (2).

The results are shown in Table 7.

EXAMPLE 32

In Example 23, 562.8 g of ammonium tungstate, 247.9 of zinc nitrate and 70.8 g of silver nitrate were added together with 812.3 g of cesium nitrate. Otherwise, as in Example 23, a slurry (o) was prepared.

In the preparation of the slurry (o), the amounts of cesium nitrate, ammonium tungstate and silver nitrate were changed to 1,056.0 g, 225.1 g and 35.4 g, respectively. Otherwise, in the same was as above, a slurry (p) was prepared.

In Example 23, instead of the pelletized carrier, a ring-like carrier composed of silica-alumina (an outside diameter of 6 mm, a length of 5 mm, a throughhole inside diameter of 3 mm) was used. First, the slurry (o) and then the slurry (p) were successively deposited each three times. Otherwise Example 23 was carried out in the same way to prepare a catalyst (9).

The amount of the catalytically active substances deposited in the catalyst (9) was 20 g per 100 ml of the carrier. After drying and calcination of the slurry (o), the composition of the oxides was as follows:

$$Mo_{12}P_{1.09}As_{0.3}V_{1.09}Cs_{1.0}W_{0.5}Zn_{0.2}Ag_{0.1}$$

After drying and calcination of the slurry (p) the composition of the oxides was as follows:

$$Mo_{12}P_{1.09}As_{0.3}V_{1.09}Cs_{1.3}W_{0.2}Zn_{0.2}Ag_{0.05}$$

Subsequently, an oxidation reaction was carried out in the same way as in Example 25 except that the catalyst (9) was used instead of the catalyst (2).

The results are shown in Table 7.

EXAMPLE 33

In Example 23, 555.0 g of thallium nitrate, 166.1 g of niobium pentoxide, 441.0 g of strontium nitrate and 96.0 g of palladium nitrate were added together with 812.3 g of cesium nitrate. Otherwise, a slurry (q) was prepared as in Example 23.

In the preparation of the slurry (q), The amounts of arsenious acid, thallium nitrate and strontium nitrate were changed to 82.5 g, 721.5 g and 617.4 g, respectively. Otherwise, a slurry (r) was prepared.

Then, in Example 23, instead of the pelletized carrier, a spherical carrier of silicon carbide (outside diameter 6 mm) was used. First, the slurry (q) was deposited and then the slurry (r) was deposited each three times. Otherwise, as in Example 23, a catalyst (10) was prepared.

The amount of the catalytically active substances in the catalyst (10) deposited was 20 g per 100 ml of the carrier. After the drying and calcining of the slurry (q), the composition of the oxides was as follows:

$$Mo_{12}P_{1.09}As_{0.3}V_{1.09}Cs_{1.0}Tl_{0.5}Sr_{0.5}Nb_{0.3}Pd_{0.1}$$

After drying and calcining of the slurry S(r), the composition of the oxides was as follows:

$$Mo_{12}P_{1.09}As_{0.2}V_{1.09}Cs_{1.0}Tl_{0.8}Sr_{0.7}Nb_{0.3}Pd_{0.1}$$

Except that the catalyst (10) was used instead of the catalyst (2), an oxidation reaction was carried out in the same way as in Example 25. The results are shown in Table 7.

EXAMPLE 34

In Example 23, 307.2 g of rubidium nitrate, 196.8 g of calcium nitrate and 135.4 g of rhodium nitrate were added together with 812.3 g of cesium nitrate. Otherwise, in the same way as in Example 23, a slurry (s) was prepared.

In the preparation of the slurry (s), the amounts of rubidium nitrate and calcium nitrate were changed to 553.0 g and 393.6 g, and otherwise, a slurry (t) was prepared in the same way as above.

Then, in Example 23, a ring-like carrier (having an outside diameter of 6 mm, a length of 5 mm and an inside diameter of 3 mm) composed of silicon carbide was used instead of the pelletized carrier. The slurry (s) and then the slurry (t) were successively deposited on these carriers by repeating the deposition operation three times. Otherwise, in the same way as in Example 23, a catalyst (11) was prepared.

The amount of the catalytically active substances in the catalyst (11) deposited was 20 g per 100 mg of the carrier.

After drying and calcination of the slurry (s), the composition of the oxides was as follows:

$$Mo_{12}P_{1.09}As_{0.3}V_{1.09}Cs_{1.0}Rb_{0.5}Ca_{0.2}Rh_{0.1}$$

After the drying and calcination of the slurry (t), the composition of the oxides was as follows:

$$Mo_{12}P_{1.09}As_{0.3}V_{1.09}Cs_{1.0}Rb_{0.4}Rh_{0.1}$$

An oxidation reaction was carried out in the same way as in Example 25 except that the catalyst (11) was used instead of the catalyst (2).

The results are shown in Table 7.

EXAMPLE 35

Molybdenum trioxide (4,320 g), 227.4 g of vanadium pentoxide and 432.5 g of 85% ortho-phosphoric acid were added to 15 liters of water, and the mixture was heated under reflux for 24 hours. Then, 215.1 g of cerium oxide, 379.2 g of potassium nitrate and 39.8 g of (powdery) copper oxide were added to prepare a slurry (u).

In the preparation of the slurry (u), the amounts of cerium oxide and copper oxide used were changed to 43.0 g and 19.9 g. Otherwise, in the same way as above, a slurry (v) was prepared.

Then, in Example 23, a pelletized carrier composed of alpha-alumina was used instead of the silicon carbide pelletized carrier. First, the slurry (u) and then the slurry (v) were successively deposited each three times to prepare a catalyst (12) in the same way as in Example 23.

The amount of the catalytically active substances in the catalyst (12) deposited was 20 g per 100 ml of the carrier. After drying and calcination of the slurry (u), the composition of the oxides was as follows:

$$Mo_{12}V_1P_{1.5}K_{1.5}Cu_{0.2}Ce_{0.5}$$

After drying and calcination of the slurry (v), the composition of the oxides was as follows:

$$Mo_{12}V_1P_{1.5}K_{1.5}Cu_{0.1}Ce_{0.1}$$

Subsequently, an oxidation reaction was carried out in the same way as in Example 25 except that the catalyst (12) was used instead of the catalyst (2).

The results are shown in Table 7.

TABLE 6

| | Catalyst No. | Carrier Type | Carrier Shape | Carrier Size (mm) *1 | Specific surface area (m²/g) | Pore volume (ml/g) | Pore diameter distribution *2 A | B | C | Reaction temperature (°C.) | Methacrolein conversion (mole %) | Methacrylic acid selectivity (mole %) | One-pass yield of methacrylic acid (mole %) |
|---|---|---|---|---|---|---|---|---|---|---|---|---|---|
| Ex. 23 | 1 | SiC | pellet | 6 × 6 | 7.1 | 0.348 | 43 | 8 | 46 | 300 | 87.3 | 86.4 | 75.4 |
| Ex. 24 | 1 | — | — | — | — | — | — | — | — | 300 | 84.8 | 86.2 | 73.1 |
| Ex. 25 | 2 | " | ring | 6 × 3 × 5 | 7.0 | 0.344 | 42 | 6 | 48 | 300 | 86.0 | 86.9 | 74.7 |

*1 Pellet = outside diameter × length; ring = outside diameter × through-hole inside diameter × length
*2 A: Proportion of pores with a pore diameter of 1–10 micrometers based on the total pore volume (%) B: Proportion of pores with a pore diameter of 0.5 to less than 1 micrometer based on the total pore volume (%) C: Proportion of pores with a pore diameter of 0.1 to less than 0.5 micrometer based on the total pore volume (%).

TABLE 7

| | Catalyst Nos. | Carrier Type | Carrier Shape | Size (mm) *1 | Reaction temperature (°C.) | Methacrolein conversion (mole %) | Methacrylic acid selectivity (mole %) | One-pass yield methacrylic acid (mole %) |
|---|---|---|---|---|---|---|---|---|
| Ex. 26 | 3 | α-alumina | ring | 6 × 3 × 5 | 310 | 84.1 | 84.0 | 70.6 |
| Ex. 27 | 4 | SiC | sphere | 6 | 310 | 81.0 | 80.7 | 65.4 |
| Ex. 28 | 5 | SiC | ring | 6 × 3 × 5 | 320 | 83.0 | 79.2 | 65.7 |
| Ex. 29 | 6 | α-alumina | pellet | 6 × 6 | 300 | 86.3 | 86.4 | 74.6 |
| Ex. 30 | 7 | α-alumina | ring | 6 × 3 × 5 | 300 | 85.5 | 81.7 | 69.9 |
| Ex. 31 | 8 | silica-alumina | pellet | 6 × 6 | 300 | 82.4 | 85.7 | 70.6 |
| Ex. 32 | 9 | silica-alumina | ring | 6 × 3 × 5 | 300 | 84.2 | 85.6 | 72.1 |
| Ex. 33 | 10 | SiC | sphere | 6 | 310 | 82.0 | 81.2 | 66.6 |
| Ex. 34 | 11 | SiC | ring | 6 × 3 × 5 | 310 | 81.9 | 81.4 | 66.7 |

TABLE 7-continued

| Catalyst Nos. | Carrier | | Size (mm) *1 | Reaction temperature (°C.) | Methacrolein conversion (mole %) | Methacrylic acid selectivity (mole %) | One-pass yield methacrylic acid (mole %) |
| --- | --- | --- | --- | --- | --- | --- | --- |
| | Type | Shape | | | | | |
| Ex. 35  12 | α-alumina | pellet | 6 × 6 | 290 | 89.2 | 81.0 | 72.3 |

*1 Pellet = outside diameter × length; ring = outside diameter × through-hole inside diameter × length; sphere = outside diameter

EXAMPLE 36

By using the catalyst (1) obtained in Example 23, a continuous reaction was carried out for 4,000 hours under the same condition as in Example 25. The initial reaction temperature was adjusted to 300° C. To obtain almost the same methacrolein conversion after 4,000 hours from the initiation of the reaction, it was sufficient to raise the reaction temperature by 7° C. The reaction results after 4,000 hours were as follows:
Reaction temperature: 307° C.
Methacrolein conversion: 84.4%
Methacrylic acid selectivity: 86.7

EXAMPLE 37

By using the catalyst (1) obtained in Example 23, isobutylaldehyde was oxidatively dehydrogenated.

Specifically, 1,500 ml of the catalyst (1) was filled in a steel reaction tube having a diameter of 25.4 mm, and a gaseous mixture composed of isobutylaldehyde:oxygen:steam:nitrogen=5.0:12.5:10.0:72.5 (by volume ratio) was introduced at a space velocity of 800 hr$^{-1}$ (STP). The reaction was carried out at a temperature of 290° C. The results are shown in Table 8.

EXAMPLE 38

By using the catalyst (1) obtained in Example 23, isobutyric acid was oxidatively dehydrogenated.

Specifically, 1,500 ml of the catalyst (1) was filled in a steel reactor having a diameter of 25.4 mm, and a gaseous mixture of isobutyric acid:oxygen:steam:nitrogen =5.0:10.0:10.0:75.0 (volume ratio) was introduced at a space velocity of 2,000 hr$^{-1}$ (STP), and reacted at a temperature of 290° C.

The results are shown in Table 9.

TABLE 8

| | Catalyst No. | Reaction temperature (°C.) | isobutylaldehyde conversion (mole %) | Selectivity (mole %) | | One-pass yield (mole %) | |
| --- | --- | --- | --- | --- | --- | --- | --- |
| | | | | Methacrylic acid | Methacrolein | Methacrylic acid | Methacrolein |
| Example 37 | 1 | 290 | 100 | 68.1 | 14.3 | 68.1 | 14.3 |

TABLE 9

| | Catalyst No. | Reaction temperature (°C.) | isobutyric acid conversion (mole %) | Selectivity (mole %) Methacrylic acid | One-pass yield (mole %) Methacrylic acid |
| --- | --- | --- | --- | --- | --- |
| Example 38 | 1 | 290 | 98.4 | 80.3 | 79.0 |

We claim:

1. A catalyst for the production of methacrylic acid composed of an inert carrier and a catalytically active substance layer deposited on the carrier, the catalytically active substance layer being composed of oxides represented by the following formula (I)

$$Mo_aP_bA_cB_dC_eD_fO_x \quad (I)$$

where Mo represents molybdenum, P represents phosphorus, A represents at least one element selected from the group consisting of arsenic, antimony, germanium, bismuth, zirconium, cerium and selenium, B is at least one element selected from the group consisting of copper, iron, chromium, nickel, manganese, cobalt, tin, silver, zinc, palladium, rhodium and tellurium, C represents at least one element selected from the group consisting of vanadium, tungsten and niobium, D represents at least one element selected from alkali metals, alkaline earth metals and thallium, and O represents oxygen, a, b, c, d, e, f and x respepectively represent the atomic ratios of Mo, P, A, B, C, D and O, and when a=12, b=0.5-4, c=0-5, d=0-3, e=0-4, f=0.01-4, and x is a numerical value determined by the oxidation states of these elements, the catalytically active substance layer being formed by preheating the inert carrier to 100° to 250° C., mixing compounds of the elemental components of the oxides of formula (I), as required, heating them to prepare a slurry or a solution, spraying the slurry or solution onto the preheated inert carrier, and calcining the inert carrier having deposited the slurry or solution thereon, said catalytically active substance layer having a specific surface area of 1 to 20 m$^2$/g, a pore volume of 0.1 to 1 ml/g, and a pore diameter distribution such that the volumes occupied by pores having pore diameter in the range of 1 to 10 micrometers is 20 to 70%.

pore diameter in the range of 0.5 to less than 1 micrometer is not more than 20%, and pore diameter in the range of 0.1 to less than 0.5 micrometer is 20 to 70%

(volume proportions based on the total pore volume).

2. A catalyst for the production of methacrylic acid according to claim 1 in which said catalytically active substance layer is of a multilayer structure consisting of at least two layers having different catalytic compositions and each layer being formed by mixing compounds containing elemental components of the oxides represented by formula (I) to form at least two slurries or solutions having different compositions, and successively spraying each said slurry or solution onto said pre-heated inert carrier, and calcining the inert carrier having deposited thereon each said slurry or solution, said catalytic compositions of said multilayer structure having a specific surface area of 1 to 20 m$^2$/g, a pore volume of 0.1 to 1 ml/g, and a pore diameter distribution such that the volumes occupied by pores having a pore diameter in the range of 1 to 10 micrometers is 20 to 70%.

a pore diameter in the range of 0.5 to less than 1 micrometer is not more than 20%, and a pore diameter in the range of 0.1 to less than 0.5 micrometer is 20 to 70% (volume proportions based on the total pore volumes).

3. A catalyst for the production of methacrylic acid according to claim 1 in which said catalytically active substance layer is of a multilayer structure consisting of at least two catalytic compositions having different layers and being formed by mixing compounds of elemental components of the oxide represented by formula (I) to form at least two or more slurries or solutions having different compositions, and successively and repeatedly spraying each of these slurries or solutions on said preheated inert carrier, and calcining the inert carrier having deposited thereon the slurries or solutions, said catalytic compositions of said multilayer structure having a specific surface area of 1 to 20 $m^2/g$, a pore volume of 0.1 to 1 ml/g, and a pore diameter distribution such that the volumes occupied by pores having a pore diameter in the range of 1 to 10 micrometers is 20 to 70%, a pore diameter in the range of 0.5 to less than 1 micrometers is not more than 20%, a pore diameter in the range of 0.1 to less than 0.5 micrometers is 20 to 70%.

* * * * *